United States Patent [19]
Felbinger et al.

[11] Patent Number: 5,825,487
[45] Date of Patent: Oct. 20, 1998

[54] PARTICLE SENSOR WITH FEATURES FOR SETTING, ADJUSTING AND TRIMMING THE FLOW RATE OF THE SAMPLED AIR

[75] Inventors: Raymond J. Felbinger, Mission Viejo; David L Chandler, Highland, both of Calif.

[73] Assignee: Venturedyne, Ltd., Milwaukee, Wis.

[21] Appl. No.: 728,209

[22] Filed: Oct. 10, 1996

[51] Int. Cl.[6] ............................ G01N 15/14; G01N 21/53
[52] U.S. Cl. ............................ 356/338; 250/576; 356/339
[58] Field of Search ................................. 356/338, 339; 250/576

[56] References Cited

U.S. PATENT DOCUMENTS

| | | | |
|---|---|---|---|
| 3,462,608 | 8/1969 | Weston et al. | 250/576 |
| 4,314,764 | 2/1982 | Liddell et al. | 356/417 X |
| 4,746,215 | 5/1988 | Gross | 356/339 |
| 5,424,558 | 6/1995 | Borden et al. | 356/338 X |
| 5,515,164 | 5/1996 | Kreikebaum et al. | 356/339 |
| 5,534,706 | 7/1996 | Borden et al. | 356/338 X |

OTHER PUBLICATIONS

Ower et al: "The measurement of air Flow", Pergamon Press Ltd, 1996, pp. 146, 147, 251, 263, 312, 313.

Primary Examiner—Vincent P. McGraw
Attorney, Agent, or Firm—Jansson, Shupe, Bridge & Munger, Ltd.

[57] ABSTRACT

Disclosed is a particle sensor of the type having (a) a light beam, (b) an air tube flowing a stream of air across the light beam at a volumetric flow rate, and (c) an air pump providing the stream of air through the tube, across the light beam and along an air flow path. In the improvement, the particle sensor includes a flow-controlling apparatus in series with the flow path for slightly trimming or adjusting the flow rate, i.e., the rate usually set at the factory before shipping. Such flow-controlling apparatus is selected from a group of apparatus including a choke valve (preferably an adjustable choke valve), a slip clutch, a speed-adjustable blower drive motor and a plurality of conduits. The conduits may have the same passage cross-sectional area and differing lengths, the same length and differing cross-sectional area or a combination of such conduits. A new method for assaying an airborne particle is also disclosed.

9 Claims, 8 Drawing Sheets

PARTICLE SENSOR WITH FEATURES FOR SETTING, ADJUSTING AND TRIMMING THE FLOW RATE OF THE SAMPLED AIR

FIELD OF THE INVENTION

This invention relates generally to air quality and, more particularly, to instruments for assaying airborne particulates.

BACKGROUND OF THE INVENTION

Particle counters and sensors are used to detect light scattered by particles entrained in a stream of fluid, e.g., in an air stream. Such counters and sensors draw air (with entrained particles) from a room, for example, and flow such air along a tube and through an illuminated sensor "view volume" to obtain information about the number and size of such particles. Such information results from an analysis of the very small amounts of light reflectively "scattered" by the particle as it moves through the view volume.

Some types of sensors flow such air along an enclosed transparent tube; others "project" the air and accompanying particles at a particular flow rate (often measured in cubic feet per minute) from one tube across an open space to another tube. In sensors of the latter type, there is no tube wall (however transparent such wall may be) to impair light scattering and collecting. In other words, the particle is briefly illuminated by a light beam as it "flies" through an open space.

Among other uses, particle counters incorporating particle sensors are used to obtain a measure of air quality by providing information as to the number and size of particles present in some specified volume of air, e.g., a cubic meter of air. Even work environments which appear to human observation to be clean—business offices, manufacturing facilities and the like—are likely to have substantial numbers of airborne particles. While such particles are not usually troublesome to the human occupants, they can create substantial problems in certain types of manufacturing operations.

For example, semiconductors and integrated chips are made in what are known as "clean rooms," the air in which is very well filtered. In fact, clean rooms are usually very slightly pressurized using extremely clean air so that particle-bearing air from the surrounding environs does not seep in. And the trend in the semiconductor and integrated chip manufacturing industry is toward progressively smaller products.

A small foreign particle which migrates into such a product during manufacture can cause premature failure or outright product rejection even before it is shipped to a customer. This continuing "miniaturization" requires corresponding improvements in clean-room environments (and in the related measuring instruments) to help assure that the number and size of airborne particles are reduced below previously-acceptable levels.

Factories making semiconductors and integrated chips are not the only sites at which particle sensors may be used. Makers of pharmaceutical products have applications for such sensors to help exclude foreign matter from medicines and drugs.

To create the flow of air used to draw particles through the sensing chamber of the particle sensor, such sensors are equipped with some type of air-moving mechanism, e.g., an air pump, downstream of the chamber and of the inlet passage leading thereto. In practice, particle sensors are factory-set at a particular flow rate. e.g., 0.7 cubic feet of air per minute (CFM), using a specified or assumed set of operating conditions. And to be reliable, data provided by the sensor must be taken at such flow rate.

But operating conditions change. And if that occurs, it becomes necessary (in order to gather reliable data) to "trim" or adjust the actual flow rate being experienced under the new conditions so that such flow rate is again equal to that set at the factory. As an example, the factory-set flow rate may be 0.7 CFM and changed operating conditions may cause such flow rate to undesirably increase to 0.75 CFM. To obtain reliable data, such flow rate must be reduced to 0.7 CFM.

Until the advent of the sensor described in the Kreikebaum et al. patent noted below, air flow through a particle sensor was by using a positive-displacement vacuum pump of the type utilizing carbon vanes, diaphragms or pistons. A manufacturer of carbon vane pumps is Gast. It is believed that the vacuum pump mentioned in U.S. Pat. No. 3,678,487 (Ludewig, Jr. et al.), which is said to cause a positive flow of gases, is a positive-displacement pump.

Positive-displacement pumps have relatively flat pressure vs. flow rate operating curves. That is, assuming a constant pump operating speed, the particle sensor inlet air flow rate caused by such pumps may be changed appreciably only by changing the pressure drop along the sensor inlet path rather dramatically. Thus, the air flow rate through a particle sensor equipped with a positive-displacement pump may be adjusted using a device which exhibits relatively high pressure drop, i.e., substantially greater than about 3 inches water at the desired flow rate.

A relatively-new way to move air through a particle sensor is with a centrifugal blower as disclosed in U.S. Pat. No. 5,515,164 (Kreikebaum et al.). A centrifugal blower is characterized by a relatively steep pressure vs. flow rate operating curve. That is, the particle sensor inlet air flow rate caused by such a blower may be changed appreciably by changing the pressure drop along the sensor inlet path only slightly. Thus, the air flow rate through a particle sensor equipped with a centrifugal blower cannot satisfactorily be adjusted using a device which exhibits relatively high pressure drop.

Another characteristic of a centrifugal blower (even the small blower used in the product disclosed in the Kreikebaum et al. patent) is that with minimal pressure drop at the blower inlet (as would result from a very-low-pressure-drop sensor inlet path), the flow rate along such path is likely to be several times the factory-set flow rate.

Because of these centrifugal blower operating characteristics, the typical requirement is to initially adjust or re-adjust the flow rate back to a factory setting. This involves increasing or decreasing the pressure drop along the inlet path, i.e., increasing or decreasing the sensor air flow rate. Until the advent of the invention, there was no known convenient, effective, low-cost way of decreasing air flow rate through a sensor having a centrifugal blower. The invention responds to this need in a unique, creative way.

OBJECTS OF THE INVENTION

It is an object of the invention to provide an improved particle sensor overcoming some of the problems and shortcomings of the prior art.

Another object of the invention is to provide an improved particle sensor having features by which the air flow rate through the sensor may be easily set and, when required, easily re-set.

Yet another object of the invention is to provide an improved particle sensor, the air flow rate through which may be adjusted either in a continuum or in discrete "steps" over a relatively-wide range.

Another object of the invention is to provide an improved particle sensor having reduced weight. How these and other objects are accomplished will become more apparent from the following descriptions and from the drawing.

SUMMARY OF THE INVENTION

The invention involves a particle sensor of the type having (a) a light beam, (b) an air tube flowing a stream of air across the light beam, and (c) an air pump drawing the stream of air through the tube, across the light beam and along an air flow path. In the improvement, the sensor includes a flow-controlling apparatus in series with the flow path for selecting the flow rate. In a highly preferred embodiment, the flow-controlling apparatus is selected from a group of apparatus including a choke valve (of any of several types) and a plurality of conduits.

In a more specific embodiment of the new particle sensor, the flow-controlling apparatus is a choke valve having an air flow opening through it. Such opening has a cross-sectional area and the choke valve includes a device for changing the cross-sectional area. The choke valve may be selected from a group of choke valves including a gate valve, a butterfly valve, a "pinch valve" and a diaphragm valve.

In another, more specific embodiment of the new particle sensor, the flow-controlling apparatus includes a group of conduits, each having an air flow passage therethrough. The passage of each conduit has a cross-sectional area differing from the cross-sectional areas of the other conduits in the group. So configured, a particular conduit may be selected to provide the needed restriction in the air flow path, thereby selecting air flow rate.

In yet another embodiment, the passage of each conduit has a cross-sectional area substantially equal to the passage cross-sectional areas of the other conduits in the group. However, the conduits in the group have differing lengths. A conduit having a particular length may be selected to provide the needed restriction in the air flow path.

Some users of the new particle sensor can do so with only rough, perhaps even "intuitive" air flow rate settings. But for certain applications, accurately-set flow rates are required. To the latter end, certain embodiments of the new particle sensor include a flow sensor ion the air flow path for determining the volumetric rate. Such flow sensor may be selected from a group of flow sensors including a mass flow sensor, a turbine, a rotameter and a differential pressure sensor.

A preferred mass flow sensor includes a temperature-coefficient (positive or negative) resistor or "thermistor" as they are sometimes called. That is, the value of the resistance changes in direct or inverse proportion to the rate of air flow across such resistor and across the light beam of the particle sensor.

Another type of suitable flow sensor is a turbine having a rotating member. The rotational speed of such member is generally proportional to the volumetric rate at which air is flowing across the light beam. Yet other types of flow sensors useful with the new particle sensor include a rotameter and a differential pressure sensor, the latter detecting air pressure at two points along the flow path.

A new method for assaying an airborne particle including the steps of providing a particle sensor having (a) a light beam, (b) an air tube flowing a stream of air across the light beam, (c) an air pump providing a stream of air through the tube, across the light beam and along an air flow path, (d) a flow sensor in the flow path for determining the volumetric rate at which air is flowing across the light beam, and (e) a flow-controlling apparatus for selecting the volumetric rate. The flow-controlling apparatus is selected from a group of apparatus as described above.

The method involves setting (otherwise referred to as "trimming") the volumetric flow rate at which air is flowing along the flow path and flowing a particle across the light beam. If the flow-controlling apparatus includes an adjustable choke valve, the setting step includes adjusting the choke valve. If the flow-controlling apparatus includes a group of conduits of the type described above as having respective passages with differing cross-sectional areas, the setting step includes installing one of the conduits in the air flow path.

If the flow-controlling apparatus includes a group of conduits of differing lengths but the same passage cross-sectional area, the setting step likewise includes installing one of the conduits in the air flow path. If the flow-controlling apparatus includes a slip-adjustable clutch, the setting step includes adjusting the coupling or "slip" of such clutch. And if the flow-controlling apparatus includes an electric motor with stator coils and Hall-effect sensors mounted for movement with respect to such coils, the setting step includes moving the sensors with respect to the coils.

Other aspects of the invention are set forth in the following detailed description and in the drawings.

DETAILED DESCRIPTION OF PREFERRED EMBODIMENTS

Figure 1:
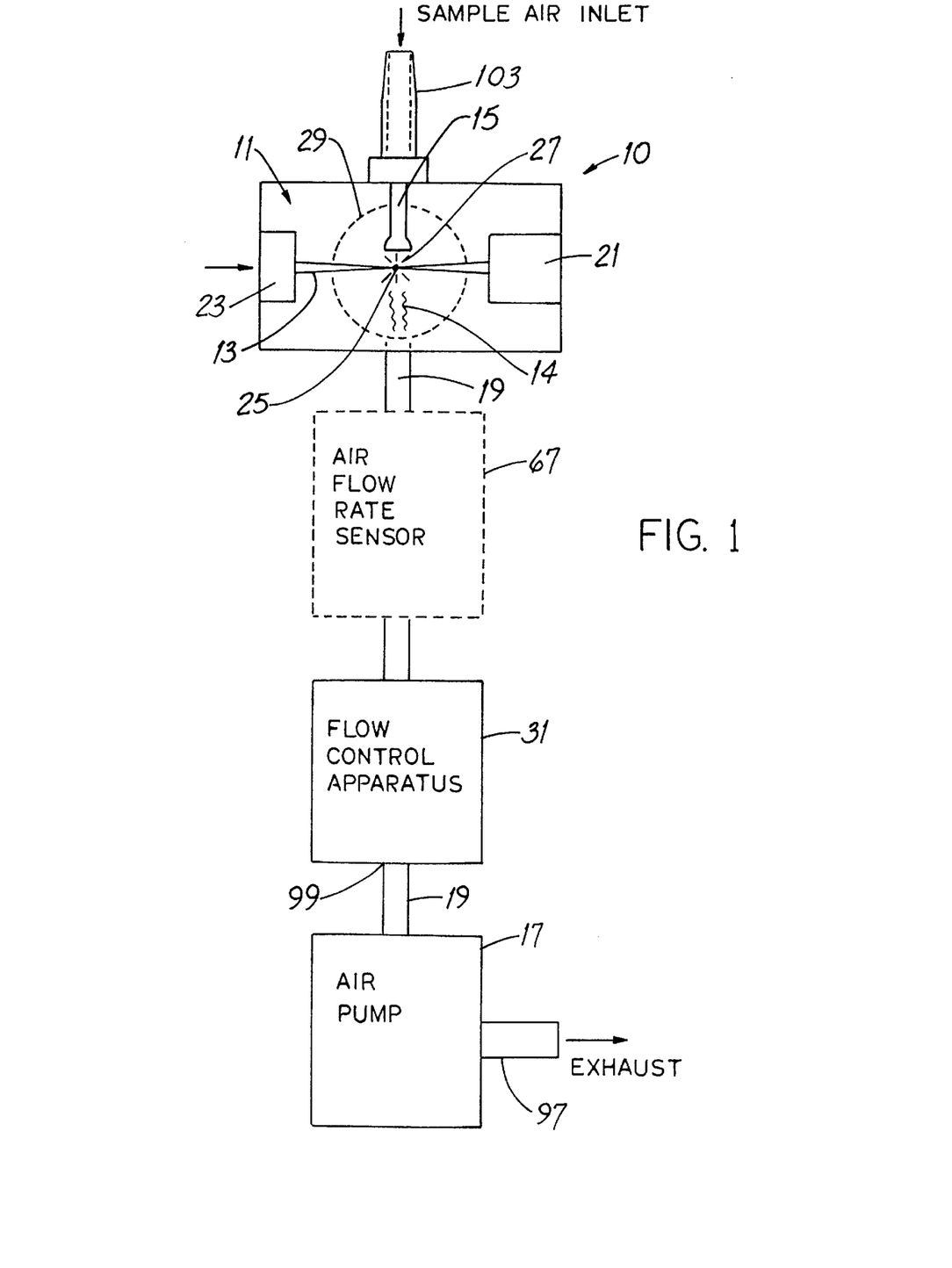
FIG. 1 is a implified diagram of the new particle sensor. The optional air flow rate sensor is shown in dashed outline.

Referring first to FIG. 1, the particle sensor 10 has a sensing section 11 with a light beam 13, an air tube 15 flowing a stream of air (represented by the lines 14) across the light beam 13, and an air pump 17 drawing the stream of air 14 through the tube 15, across the light beam 13 and along an air flow path 19. The light beam 13 emanates from a light source 21 having (typically) a laser beam and focusing optics. The light beam 13 is captured or "sunk" in a light trap 23.

A particle 25 in the stream of air flows across the light beam 13 and reflects light 27. Such light 27 is gathered by the collection optics (represented by the circle 29) and directed to appropriate detector(s) and electrical circuitry for analysis.

Figure 12:
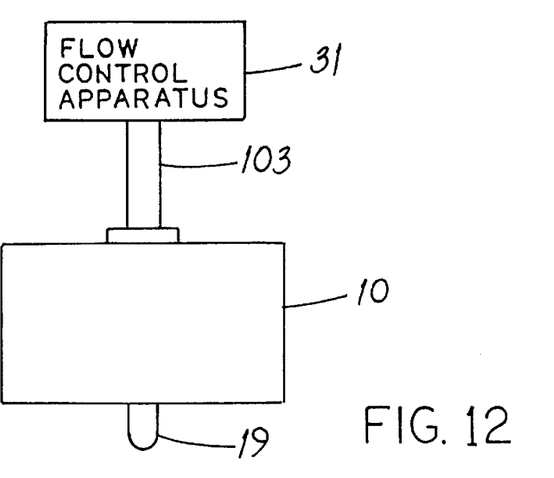
FIG. 12 a representation of a flow sensor having a flow control apparatus at the sensor sample air inlet.

The particle sensor 10 includes a flow-controlling apparatus 31 in series with the flow path 19 for setting the flow rate. Such apparatus 31 is preferably selected from a group of apparatus including, e.g., one or plural types of choke valves 33. (Noting FIG. 12, the apparatus 31 may be mounted at the sample air inlet 103 with nominally equal effect.)

Figure 2:
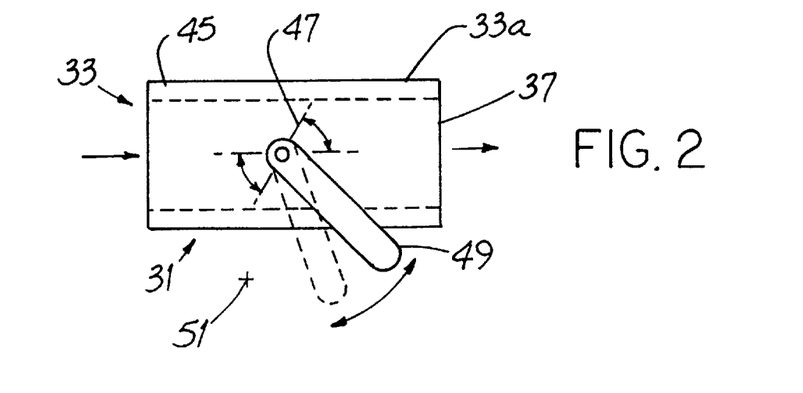
FIG. 2 is a representative side elevation view of a choke valve embodied as a butterfly valve. Surfaces of parts are shown in dashed outline.
Figure 3A:
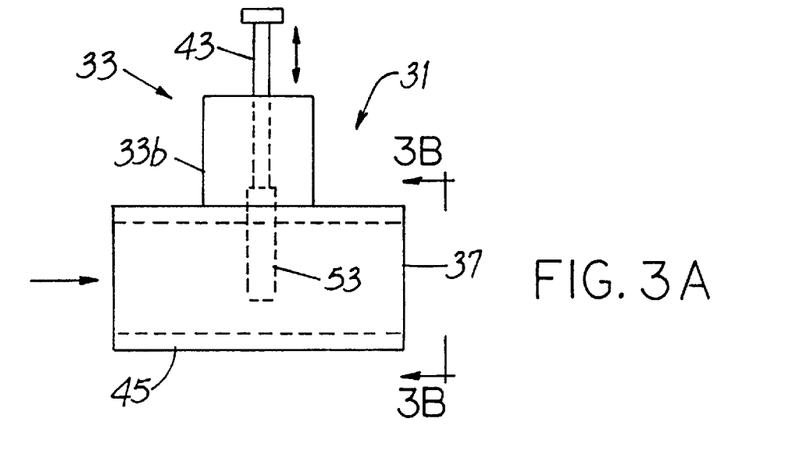
FIG. 3A is a representative side elevation view of a choke valve embodied as a gate valve. Surfaces of parts are shown in dashed outline.
Figure 3B:
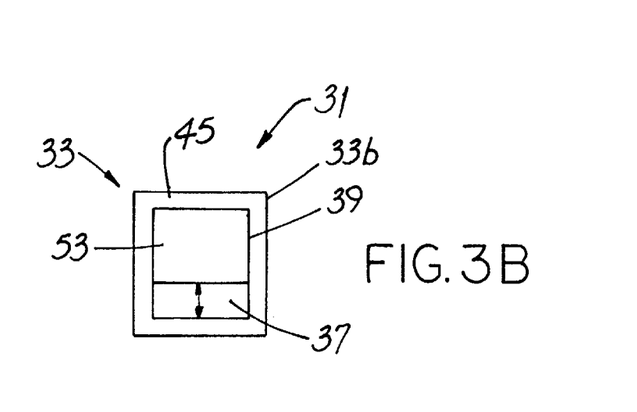
FIG. 3B an end elevation view of the body and gate of the valve of FIG. 3A taken along the viewing plane 3B—3B thereof.
Figure 4:
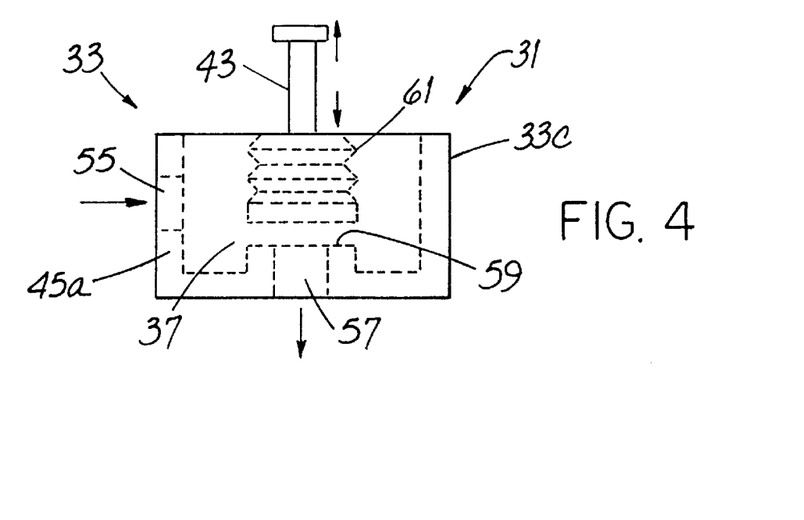
FIG. 4 is a representative side elevation view of a choke valve embodied as a diaphragm valve. Surfaces of parts are shown in dashed outline.
Figure 5:
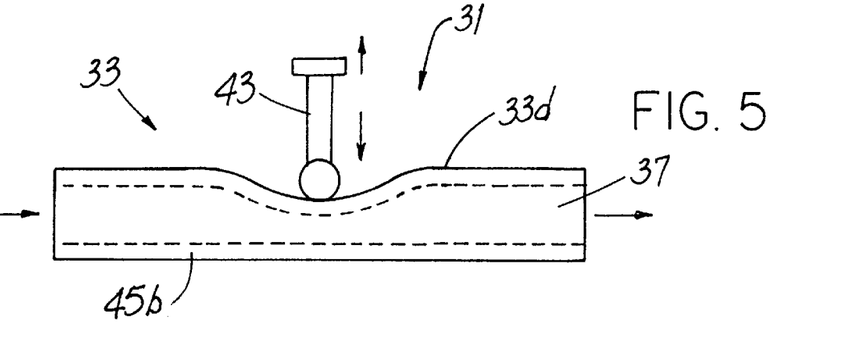
FIG. 5 is a representative side elevation view of a choke valve embodied as a pinch valve. Surfaces of parts are shown in dashed outline.

Referring next to FIGS. 1, 2, 3A, 3B, 4 and 5, one type of preferred flow-controlling apparatus is a choke valve 33a, 33b, 33c or 33d, respectively. Each such choke valve 33a, 33b, 33c, 33d has an air flow opening 37 through it and the opening 37 has a cross-sectional area. As an example, the maximum cross-sectional area of the opening 37 of choke valve 33b in FIGS. 3A and 3B is circumscribed by the line 39. Most preferably, each such choke valve 33 includes a device 43 for changing the cross-sectional area. The choke valve may be selected from a group of choke valves including a butterfly valve 33a (FIG. 2), a gate valve 33b (FIGS. 3A, 3B), a diaphragm valve 33c (FIG. 4) and a "pinch valve" 33d (FIG. 5).

The butterfly valve 33a of FIG. 2 includes a rigid body 45 through which the opening 37 is formed. A plate 47 is mounted for pivoting movement using a lever 49 or the like.

Such plate 47 has a size and shape generally conforming to that of the opening 37.

By manipulating the lever 49 between the fullyclosed position shown in solid outline and the full open position (represented by the marker 51) and when doing so, passing through the partially-open position shown in dashed outline, one may adjust the effective cross-sectional area of such opening 37. In so doing, the volumetric flow rate of air flowing along the flow path 19 and through the light beam 13 is changed.

The gate valve of FIGS. 3A and 3B also has a rigid body 45 with an opening 37 therethrough. Mounted on the body 45 is the device 43 which may be manipulated upwardly or downwardly to move the gate 53 in the body 45 and change the cross-sectional area of such opening 37.

Like the valves 33a, 33b, described above, the diaphragm valve 33c of FIG. 4 has an inlet port 55 and an outlet port 57. Within the body 45a is a seat 59 (e.g., a circular seat) against which a movable diaphragm 61 may be pressed to totally close the valve 33c. If the device 43 is manipulated to move the diaphragm 61 away from the seat 59, the effective cross-sectional area of the opening 37 is changed.

The pinch valve 33d shown in FIG. 5 has a flexible body 45b made of relatively soft tubing having an opening 37 therethrough. By manipulating the device 43 downwardly to "pinch" the body 45b and partially or totally occlude opening 37, air flow rate may be adjusted. Similarly, if the body 45b is pinched partially closed, the air flow rate is adjusted by manipulating the device 43 upwardly.

Each of the valves 33a–33d described above is characterized by the fact that the valve cross-sectional area may be changed in a continuum. That is, such cross-sectional area may be changed in a manner to be substantially free of discrete "steps" of area change. (Considered another way, one may say that the valves 33a–33d have an infinite number of adjustment steps available.)

Figure 6:
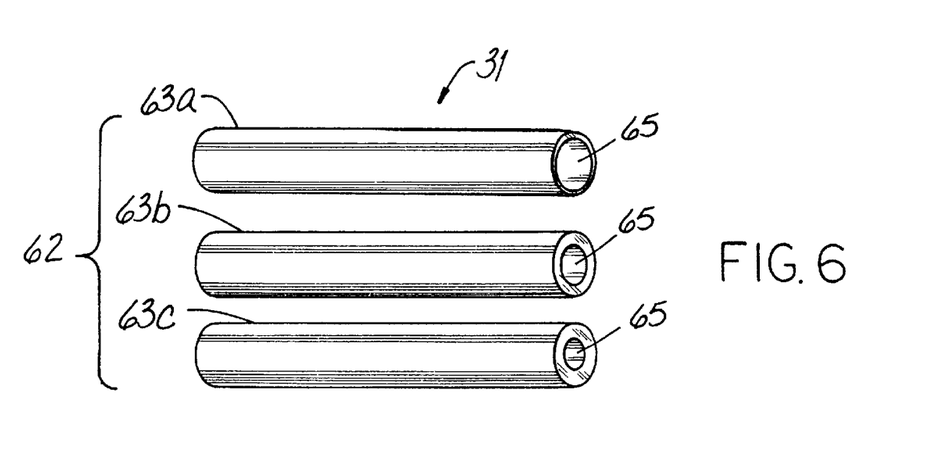
FIG. 6 is a representative perspective view of a group of conduits that may be used as the flow control apparatus of FIG. 1.
Figure 7:
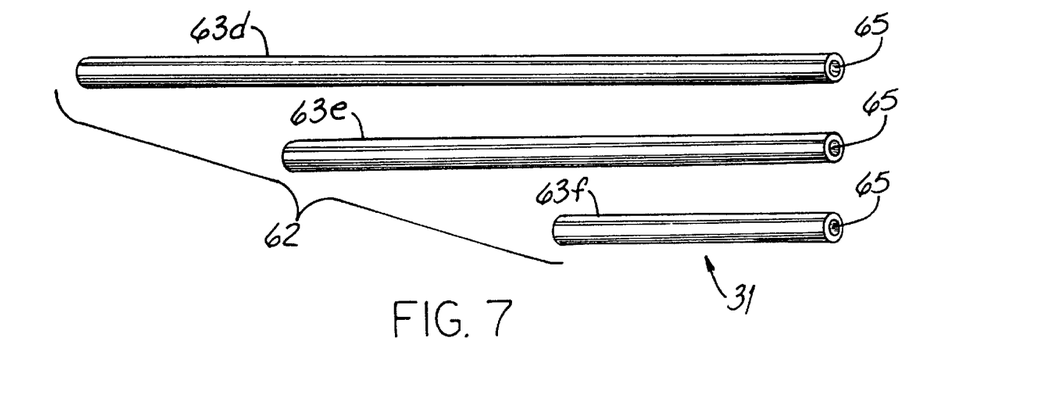
FIG. 7 is a representative perspective view of another group of conduits that may be used as the flow control apparatus of FIG. 1.

However, using a choke valve 33 is not the only way to change the air flow rate in the new particle sensor 10. Referring next to FIGS. 1, 6 and 7, the flow-controlling apparatus 31 may include a group 62 of conduits 63a, 63b, 63c or 63d, 63e, 63f each having an air flow passage 65 therethrough. In the group of conduits 63a–63c of FIG. 6, the passage 65 of each conduit 63a, 63b, 63c has a cross-sectional area differing from the cross-sectional areas of the other conduits 63a, 63b, 63c in the group 62. So configured, a particular conduit 63a, 63b or 63c may be selected to provide the needed restriction in the air flow path 19, thereby setting air flow rate.

It is to be appreciated that the group 62 may comprise only a few conduits 63a–63c (three, as an example) or a relatively-large number thereof, e.g., twenty or thirty. The larger the number of conduits 63 (assuming each has a passage cross-sectional area differing from that of all other conduits 63), the smaller will be the "steps" of change in air flow rate that may be achieved.

In the embodiment of FIG. 7, the passage 65 of each conduit 63d, 63e, 63f has a cross-sectional area substantially equal to the passage cross-sectional areas of the other conduits 63d, 63e, 63f in the group 62. However, the conduits 63d, 63e, 63f in the group 62 have lengths which differ from one another. A conduit 63d, 63e or 63f having a particular length may be selected to provide the needed restriction in the air flow path 19. As noted above, the larger the number of conduits 63 with uniquely-different lengths, the smaller will be the steps of change in air flow rate that may be achieved.

From the foregoing, it is to be appreciated that an air flow rate may be set by imposing no restriction (for maximum flow rate) or some degree of restriction, from modest to severe, in the flow path 19. The valves 33 and conduit groups 62 avail a user of the ability to choose whether or not to impose such a restriction.

Some users of the new particle sensor 10 can employ such sensor 10 with only rough, perhaps even "intuitive," air flow rate settings. But for certain applications, accurately-set flow rates are required.

Figure 9:
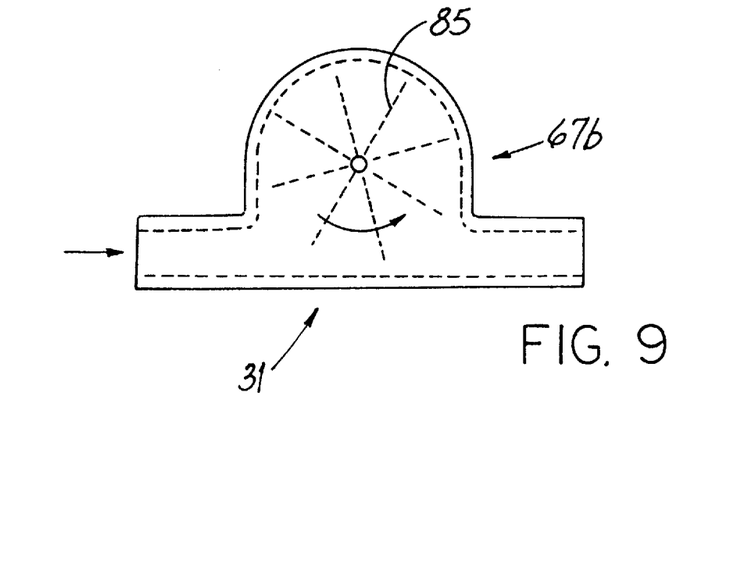
FIG. 9 is a representative side elevation view of a flow sensor embodied as a turbine flow sensor. Surfaces of parts are shown in dashed outline.
Figure 10:
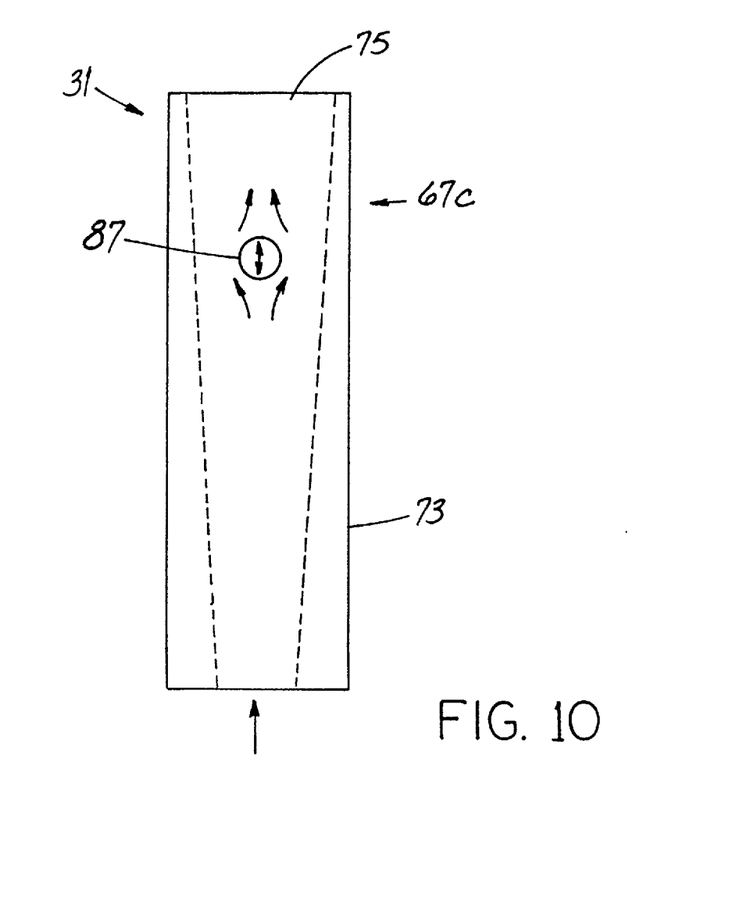
FIG. 10 is a representative side elevation view of a flow senor embodied as a rotameter. Surfaces of parts are shown in dashed outline and the taper of the air flow channel is exaggerated.
Figure 11A:
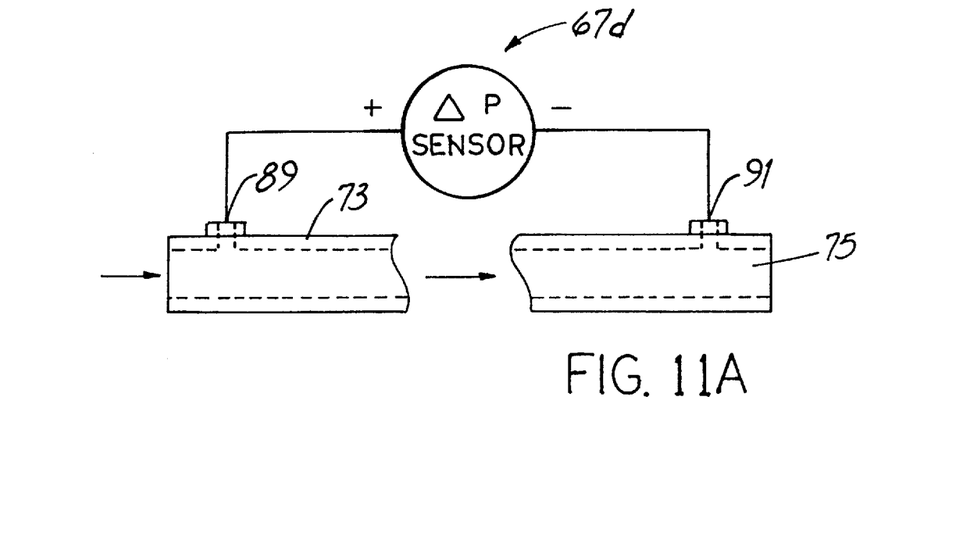
FIG. 11A presents a flow measurement device of the differential pressure type. Parts are broken away and surfaces of parts are shown in dashed outline.
Figure 11B:
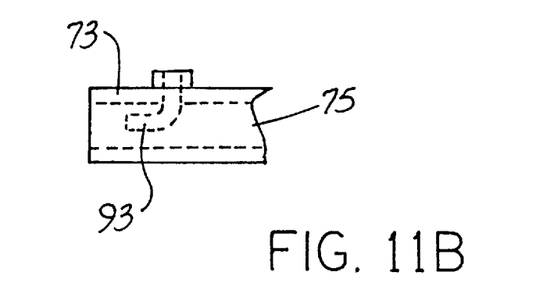
FIG. 11B represents a pitot tube which may be used in the device of FIG. 11A. Parts are broken away and surfaces of parts are shown in dashed outline.
Figure 11C:
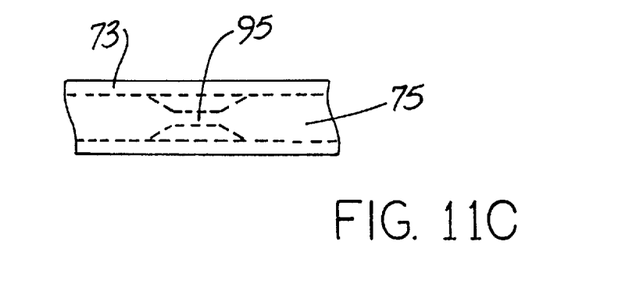
FIG. 11C is a series restrictor which may be used in the device of FIG. 11A. Parts are broken away and surfaces of parts are shown in dashed outline.

Referring next to FIGS. 1, 8A, 8B, 9, 10, 11A–C, certain embodiments of the new particle sensor 10 include a flow sensor 67 in the air flow path 19 for determining the volumetric airflow rate. Such flow sensor 67 may be selected from a group of flow sensors 67 including a mass flow sensor 67a (FIGS. 8A, 8B), a turbine 67b (FIG. 9), a rotameter 67c (FIG. 10) and a differential pressure sensor 67d (FIGS. 11A–C).

Figure 8A:
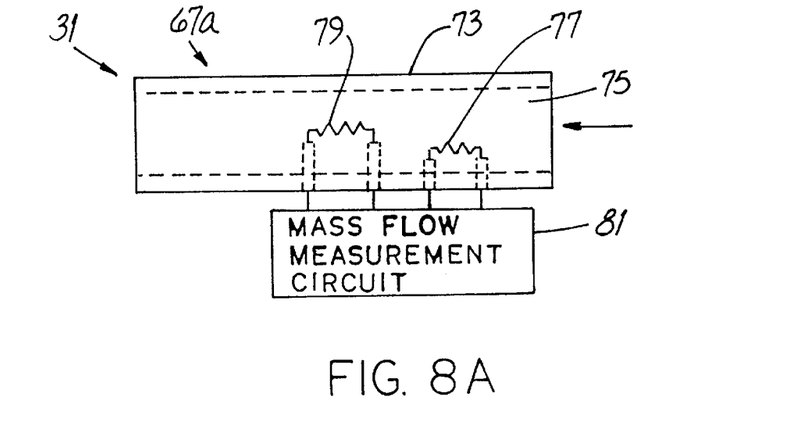
FIG. 8A is a representative side elevation view of a flow sensor embodied as a mass flow sensor. Surfaces of parts are shown in dashed outline.
Figure 8B:
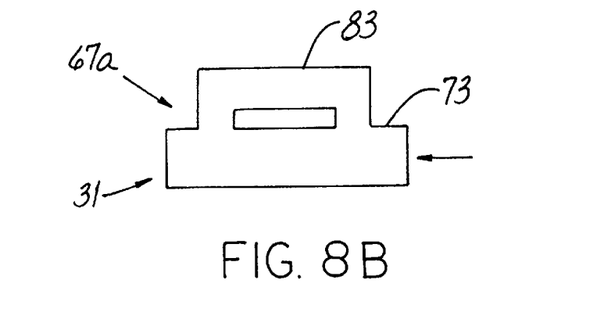
FIG. 8B is a simplified, representative side elevation view of an embodiment of the mass flow sensor of FIG. 8A and including an air flow bypass shunt.

The mass flow sensor 67a of FIG. 8A includes a rigid body 73 having an air flow channel 75 therethrough. Positioned in the channel 75 is a thermistor 77 for measuring ambient temperature and a heated thermistor 79, the instantaneous temperature of which is used to compute mass flow rate. Computation of such rate is by a measurement circuit 81. Referring to FIG. 8B, because the maximum flow capacity of suitable mass flow sensors 67a is relatively modest, a shunt 83 may be used to bypass a substantial portion of the flow around the thermistors 77, 79.

Referring next to FIG. 9, another type of suitable flow sensor is a turbine 67b having a rotating member 85 resembling a paddle wheel. The rotational speed of such member 85 is generally proportional to the volumetric rate at which air is flowing across the light beam 13 and through the turbine 67b.

Referring next to FIG. 10, yet another type of flow sensor 67 useful with the new particle sensor 10 is a rotameter 67c. Such rotameter 67c has an upright, rigid, transparent body 73 with an air flow channel 75 therethrough. Such channel 75 is tapered in that its cross-sectional area gradually increases in the upward direction. A sphere 87 is in the channel 75 and the height to which the sphere 87 rises while air flows in the channel 75 is an indication of air flow rate. The most useful type of rotameter 67c is calibrated along the body 73 in units of flow rate, e.g., increasing fractions of a cubic foot per minute.

FIG. 11A shows a flow sensor 67d of the differential pressure type, i.e., a flow sensor 67d which detects air pressure at two points 89, 91 along the channel through the body 73. The greater the difference between such pressures, the higher the flow rate. As shown in FIG. 11B, the differential pressure sensor 67d may be equipped with an "upstream-pointing" pitot tube 93 in the channel 75. And as shown in FIG. 11C, such sensor 67d may have a restrictive orifice 95 in the channel 75.

Figure 13:
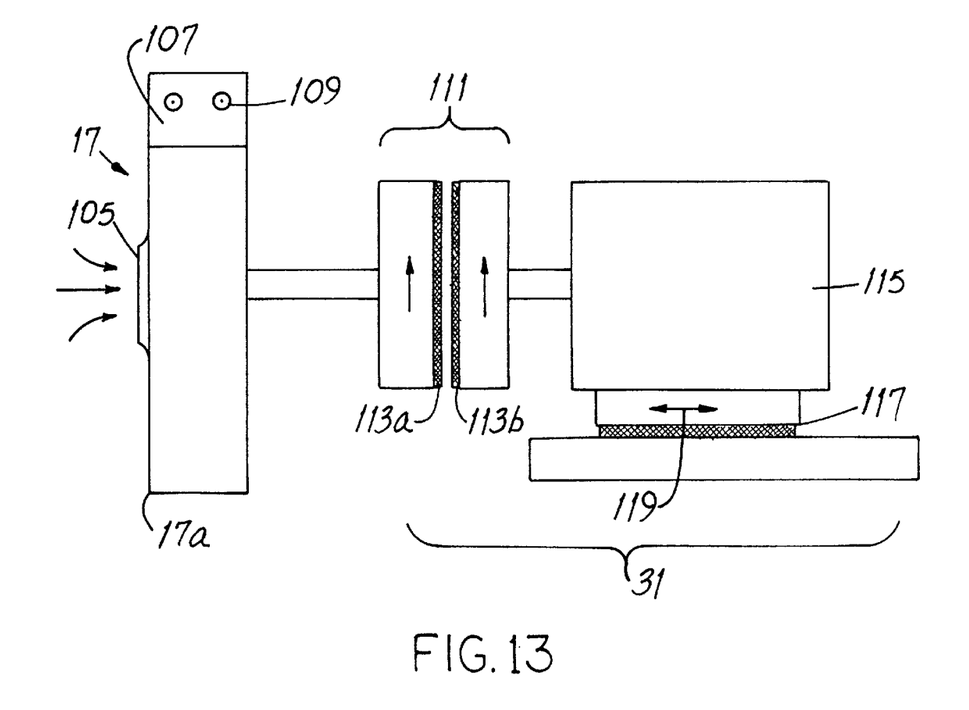
FIG. 13 is a representative view of a sensor centrifugal lower powered through an adjustable clutch by a motor. A surface of a part is shown in dashed outline.

And as comprehensive as they are, the foregoing arrangements for setting air flow rate are among others available. FIG. 13 shows an edge view of an air pump 17 embodied as a centrifugal blower 17a. Such blower 17a has an intake port 105 and an air discharge port 107.

It is to be appreciated that if the blower 17a is downstream of the sensor 10 as shown in FIG. 1, the air flow path 19 is connected to the intake port 105. If the blower 17a is upstream of the sensor 10 as in FIG. 12, the discharge port 107 is connected to the sample air inlet 103. Air flow out of the port 107 is as indicated by the arrows 109, i.e., toward the viewer of FIG. 13. Attachment of the blower 17a at either the air inlet 103 or downstream of the sensing section 11 provides the necessary stream of air.

The blower 17a is powered through a slip-adjustable clutch 111 by an electric motor 115. The clutch 111 has two engagement faces 113a, 113b. Such motor 115 is mounted on a sliding mount 117 so that the position of such motor 115 is adjustable left-to-right as indicated by the arrows 119. Adjustment of the position of the motor 115 permits one to urge face 113b against face 113a with greater or lesser force, thereby changing the amount of clutch coupling, changing the drive speed of the blower 17a and, thus, changing the rate of air flow through the sensor 10.

Figure 14:
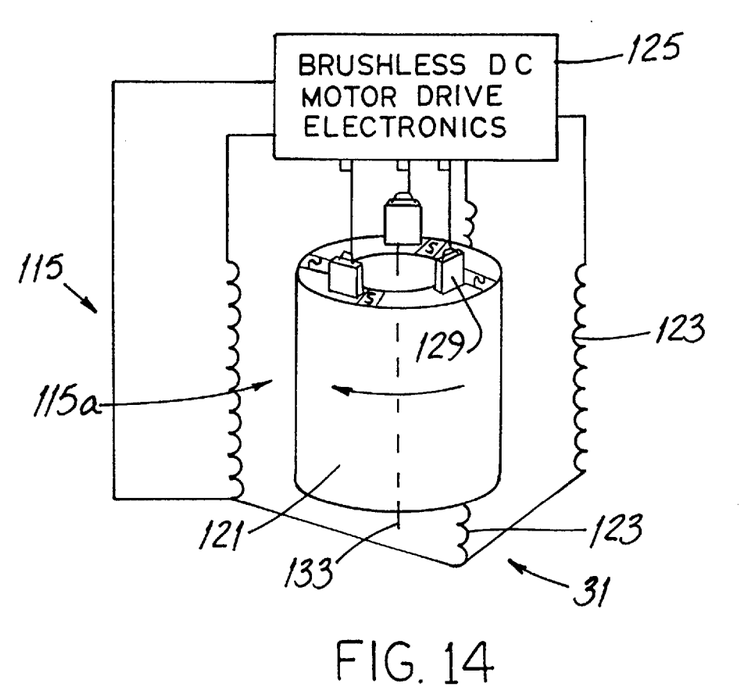
FIG. 14 is a perspective representation of stator coils of a brushless DC motor, the motor controller and a mechanism having Hall-effect sensors thereon and mounted for movement with respect to the coils.
Figure 15:
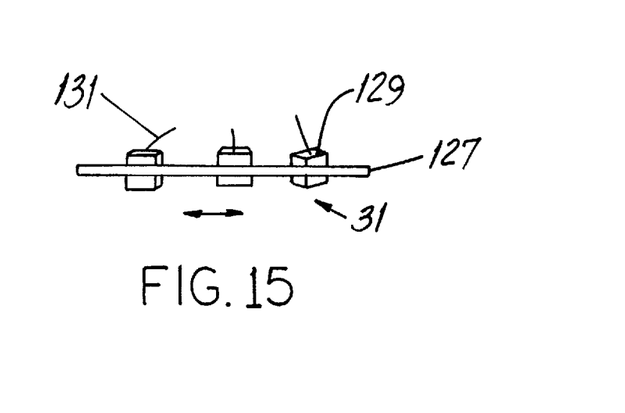
FIG. 15 is a representative side elevation view of the Hall-effect sensors shown in FIG. 14 and mounted on a plate for slight rotational movement.

Yet another way to change the rate of air flow is by changing the speed of the motor 115. Such motor 115 may be coupled to the blower 17a through the clutch 111 or, more preferably, directly, i.e., without using such clutch 111. Referring to FIGS. 14 and 15, the motor 115 is a brushless DC motor 115a having a polarized, rotating armature 121 and three stator coils 123. The electronic controller for the motor 115a is represented by the symbol 125.

The motor 115a is equipped with an annular plate-like ring 127 (not shown in FIG. 14) on which are mounted three Hall-effect sensors 129. Electrical leads 131 extend between the sensors 129 and the controller 125. The speed of the motor 115a may be changed by rotating the ring 127 with respect to the armature axis of rotation 133 and thereby changing the phase angle of the sensors 129 relative to the coils 123. (It is to be appreciated that neither the ring 127 nor the sensors 129 rotate with the armature 121. Rather, the ring 127 and sensors 129 are rotatable around the axis 133 through a small arc. From the foregoing, it should be apparent that using a slip-adjustable clutch 111 or a motor with positionable sensors 129, the air flow rate may be changed in a continuum rather than in discrete steps.

(Brushless DC motors with stationary Hall-effect sensors are, per se, known. But insofar is as known, there are no such motors capable of being speed-adjusted by manipulating the position of such sensors. Nor has a speed-adjustable brushless DC motor known to have been used on a particle sensor 10.)

Other aspects of the invention involve a new method for assaying an airborne particle 25. Such method includes the steps of providing a particle sensor 10 having (a) a light beam 13, (b) an air tube 15 flowing a stream of air 14 across the light beam 13, (c) an air pump 17 providing a stream of air 14 through the tube 15, across the light beam 13 and along an air flow path 19, (d) a flow sensor 67 in the flow path 19 for determining the volumetric rate at which air is flowing across the light beam 13, and (e) a flow-controlling apparatus 31 for setting the volumetric air flow rate. The flow-controlling apparatus 31 is selected from a group of apparatus 31 as described above. The method involves setting the volumetric flow rate at which air is flowing along the flow path 19 and flowing a particle 25 across the light beam 13.

If the flow-controlling apparatus 31 includes an adjustable choke valve 33, the setting step includes adjusting the choke valve 33. If the flow-controlling apparatus 31 includes a group 62 of conduits 63a–63c of the type described above as having respective passages 65 with differing cross-sectional areas, the setting step includes installing one of the conduits 63a, 63b or 63c in the air flow path 19. If the flow-controlling apparatus 31 includes a group of conduits 63d, 63e, 63f of differing lengths but the same passage cross-sectional area, the setting step likewise includes installing one of the conduits 63d, 63e, 63f in the air flow path.

If the flow-controlling apparatus 31 includes an adjustable clutch 111, the setting step includes adjusting the coupling or "slip" of such clutch 111. And if the flow-controlling apparatus 31 includes an electric motor 115a with stator coils 123 and Hall-effect sensors 129 mounted for movement with respect to such coils 123, the setting step includes moving the sensors 129 with respect to the coils 123.

When considering FIG. 2, it should be understood that the flow-controlling apparatus 31, the air pump 17 and (if used) the flow rate sensor 67 are in series in the air flow path 19 and may be placed in any order along such flow path 19. Of course, if the air pump 17 precedes, e.g., the flow-controlling apparatus 31, such apparatus 31 is coupled to the port 97 and the outlet port 99 of the apparatus 31 becomes the exhaust port.

Assuming appreciation of the foregoing, the following will aid understanding of ways in which the new sensor 10 can be used. A particle sensor is normally set at the factory to provide a particular air flow rate for a particular application. But it may become necessary to later "trim" or set such flow rate by making a small change in such rate. This is so because the sensor 10 may "drift" and lose its flow rate calibration and/or the sensor 10 may be used on a different application requiring a somewhat-different flow rate.

As an example of how a flow-controlling apparatus 31 may be used to set air flow rate along the path 19, in a specific sensor 10, a specific centrifugal blower 17a provides an air flow rate of about 1.0 cubic feet per minute when the pressure drop along the path 19 is 9.6 inches water. But when such pressure drop is reduced to 9.4 inches water, the air flow rate rises to about 2.0 cubic feet per minute.

It is anticipated that under most circumstances requiring re-setting air flow rate, only a modest change in pressure drop, e.g., 0.2 inches water, along the flow path 19 will be required. However, this should not be interpreted to mean that the apparatus 31 is only capable of effecting such modest changes.

While the principles of the invention have been described in connection with a few preferred embodiments, it is to be understood clearly that such embodiments are by way of example and are not limiting.

What is claimed:

1. In a particle sensor having (a) a light beam, (b) an air tube flowing a stream of room ambient air across the light beam at a volumetric flow rate, and (c) an air pump providing the stream of air through the tube, across the light beam and along an air flow path, the improvement wherein the particle sensor includes:
    a flow-controlling apparatus in series with the flow path for setting the flow rate to a particular value of the volumetric flow rate, such flow-controlling apparatus being downstream of the light beam and including a plurality of conduits, and wherein;
    each of the conduits of the plurality of conduits have a passage therethrough;
    each conduit has a length and the passage of each conduit is of uniform cross-section area along the conduit length; and
    the cross-sectional area of the passage of each conduit differs from the cross-sectional areas of the passages of the other conduits of the plurality of conduits;
and wherein:
    the flow-controlling apparatus is between the pump and the sensor.

2. In a particle sensor having (a) a light beam, (b) an air tube flowing a stream of room ambient air across the light beam at a volumetric flow rate, (c) a blower providing the stream of air through the tube, across the light beam and along an air flow path, and wherein the blower is driven by a motor having armature coils, the improvement wherein the particle sensor includes:
    a flow-controlling apparatus in series with the flow path for setting the flow rate to a particular value of the volumetric flow rate, such flow-controlling apparatus being downstream of the light beam and including at least one Hall-effect sensor positionably-adjustable in phase angle with respect to such coils.

3. A method for assaying an airborne particle entrained in room ambient air flowing into a particle sensor and including the steps of:
    configuring the particle sensor to have (a) a light beam, (b) an air tube flowing a stream of air across the light beam, (c) an air pump providing the stream of air through the tube, across the light beam and along an air flow path, (d) a flow sensor in the flow path for determining the volumetric rate at which air is flowing across the light beam, and (e) a flow-controlling apparatus for trimming air flow to a particular value of the volumetric rate, such flow-controlling apparatus comprising a plurality of conduits;
    selecting the particular value of the volumetric flow rate at which air is flowing along the flow path; and
    flowing a particle across the light beam,
and wherein:
    the plurality of conduits includes a group of conduits, each having a length of and a passage therethrough, (b) the passage of each conduit has a cross-sectional area substantially equal to the passage cross-sectional areas of the other conduits in the group, (c) the conduits in the group having differing lengths, and (d) the selecting step includes installing one of the conduits in the air flow path.

4. A method for assaying an airborne particle entrained in room ambient air flowing into a particle sensor and including the steps of:
    configuring the particle sensor to have (a) a light beam, (b) an air tube flowing a stream of air across the light beam, (c) an air pump providing the stream of air through the tube, across the light beam and along an air flow path, (d) a flow sensor in the flow path for determining the volumetric rate at which air is flowing across the light beam, and (e) a flow-controlling apparatus for trimming air flow to a particular value of the volumetric rate;
    selecting the particular value of the volumetric flow rate at which air is flowing along the flow path; and
    flowing a particle across the light beam,
and wherein:
    the flow-controlling apparatus comprises a plurality of conduits, each having a length and a passage therethrough;
    the passage of each conduit has a cross-sectional area which is substantially uniform along the conduit length; and
    the cross-sectional area of each conduit passage differs from the cross-sectional areas of the passages through the other conduits,
and wherein:
    the setting step includes installing one of the conduits in the air flow path.

5. A method for assaying an airborne particle drawn from room ambient air into a particle sensor and including the steps of:

configuring the particle sensor to have (a) a light beam, (b) an air tube flowing a stream of air across the light beam, (c) a motor-driven air pump providing a stream of air through the tube, across the light beam and along an air flow path, (d) a flow sensor in the flow path for determining the volumetric rate at which air is flowing across the light beam, and (e) a flow-controlling apparatus for trimming air flow to a particular value of the volumetric rate, such flow-controlling apparatus being selected from a group of apparatus consisting of a choke valve, a plurality of conduits and a slip-adjustable clutch between the air pump and the drive motor;

selecting the particular value of the volumetric flow rate at which air is flowing along the flow path; and flowing a particle across the light beam;

and wherein:

the selecting step includes adjusting the slip of the clutch.

6. A method for assaying an airborne particle drawn from room ambient air into a particle sensor and including the steps of:

configuring the particle sensor to have (a) a light beam, (b) an air tube flowing a stream of air across the light beam, (c) an air pump providing a stream of air through the tube, across the light beam and along an air flow path, (d) a flow sensor in the flow path for determining the volumetric rate at which air is flowing across the light beam, (e) a motor driving the air pump and having armature coils, and (f) a flow-controlling apparatus for trimming air flow to a particular value of the volumetric rate, such flow-controlling apparatus being selected from a group of apparatus consisting of a choke valve, a plurality of conduits and at least one Hall-effect sensor positionably-adjustable in phase angle with respect to the armature coils;

selecting the particular value of the volumetric flow rate at which air is flowing along the flow path; and flowing a particle across the light beam;

and wherein:

the selecting step includes adjusting the position of the Hall-effect sensor.

7. In a particle sensor having (a) a light beam, (b) an air tube flowing a stream of air across the light beam at a volumetric flow rate, (c) an air pump providing the stream of air through the tube, across the light beam and along an air flow path, and (d) a motor driving the air pump and having armature coils, the improvement wherein the particle sensor includes:

a flow-controlling apparatus for setting the flow rate to a particular value of the volumetric flow rate, such flow-controlling apparatus including at least one Hall-effect sensor positionably-adjustable in phase angle with respect to the armature coils.

8. A method for assaying an airborne particle including the steps of:

configuring the particle sensor to have (a) a light beam, (b) an air tube flowing a stream of air across the light beam, (c) an air pump providing a stream of air through the tube, across the light beam and along an air flow path, (d) a flow sensor in the flow path for determining the volumetric rate at which air is flowing across the light beam, (e) a motor driving the air pump and having armature coils, and (e) a flow-controlling apparatus for trimming air flow to a particular value of the volumetric rate, such flow-controlling apparatus consisting of at least one Hall-effect sensor positionably-adjustable in phase angle with respect to the armature coils;

selecting, by adjusting the position of the Hall-effect sensor, the particular value of the volumetric flow rate at which air is flowing along the flow path; and flowing a particle across the light beam.

9. In a particle sensor having (a) a light beam, (b) an air tube flowing a stream of room ambient air across the light beam at a volumetric flow rate, and (c) an air pump providing the stream of air through the tube, across the light beam and along an air flow path, the improvement wherein the particle sensor includes:

a flow-controlling apparatus in series with the flow path for setting the flow rate to a particular value of the volumetric flow rate, such flow-controlling apparatus being downstream of the light beam and including a plurality of conduits;

each of the plurality of conduits has a length and a passage therethrough;

the passage of each conduit has a cross-sectional area substantially equal to the passage cross-sectional areas of the other conduits of the plurality; and the conduits comprising the plurality have differing lengths.

* * * * *